(12) United States Patent
Joseph et al.

(10) Patent No.: US 11,047,870 B2
(45) Date of Patent: Jun. 29, 2021

(54) PHOTOMETRIC CUVETTE MAPPING

(71) Applicant: Siemens Healthcare Diagnostics Inc., Tarrytown, NY (US)

(72) Inventors: Joson K. Joseph, Bear, DE (US); Bestin Abraham, Newark, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 180 days.

(21) Appl. No.: 16/319,282

(22) PCT Filed: Jul. 19, 2017

(86) PCT No.: PCT/US2017/042930
§ 371 (c)(1),
(2) Date: Jan. 18, 2019

(87) PCT Pub. No.: WO2018/017760
PCT Pub. Date: Jan. 25, 2018

(65) Prior Publication Data
US 2019/0242918 A1 Aug. 8, 2019

Related U.S. Application Data

(60) Provisional application No. 62/365,287, filed on Jul. 21, 2016.

(51) Int. Cl.
*G01N 35/00* (2006.01)
*G01N 21/13* (2006.01)
(Continued)

(52) U.S. Cl.
CPC ...... *G01N 35/00712* (2013.01); *B01L 3/5085* (2013.01); *B01L 9/06* (2013.01);
(Continued)

(58) Field of Classification Search
CPC .......... H02S 20/32; H02S 20/10; H02S 20/30; H02S 40/22; F24S 30/452; F24S 40/85;
(Continued)

(56) References Cited

U.S. PATENT DOCUMENTS 4,549,809 A 10/1985 Minekane et al.
5,061,446 A 10/1991 Guigan
(Continued)

FOREIGN PATENT DOCUMENTS

CN 1839434 A 9/2006
CN 101008616 A 8/2007
(Continued)

OTHER PUBLICATIONS

PCT International Search Report and Written Opinion dated Nov. 14, 2017 (11 Pages).
(Continued)

*Primary Examiner* — Tony Ko

(57) ABSTRACT

A computer-implemented method for performing photometric cuvette mapping includes detecting edges associated with a plurality of gaps between a plurality of vessels in a reaction ring during a complete rotation of a reaction ring. Each gap is determined according to an edge detection process which includes identifying: a vessel interior in response to detection of a first predetermined number of photometer device control manager (DCM) measurements below a threshold value; a rising edge in response to detection of a second predetermined number of photometer DCM measurements above the threshold value; and identifying a falling edge in response to detection of a third predetermined number of photometer DCM measurements below the threshold value. The edge detection process further includes recording the rising edge and the falling edge as being indicative of one of the plurality of gaps.

18 Claims, 18 Drawing Sheets

(51) Int. Cl.
*G01N 35/02* (2006.01)
*B01L 9/06* (2006.01)
*G01N 21/25* (2006.01)
*B01L 3/00* (2006.01)
*G01N 35/04* (2006.01)
*A61B 5/1455* (2006.01)

(52) U.S. Cl.
CPC ........... *G01N 21/13* (2013.01); *G01N 21/253* (2013.01); *G01N 35/00663* (2013.01); *G01N 35/025* (2013.01); *G01N 35/04* (2013.01); *A61B 5/14557* (2013.01); *B01L 2200/028* (2013.01); *B01L 2300/0803* (2013.01); *G01N 2035/0444* (2013.01); *G01N 2201/025* (2013.01); *G01N 2201/0415* (2013.01)

(58) Field of Classification Search
CPC ............. F24S 2025/01; F24S 2025/012; F24S 2025/014; F24S 2030/115; F24S 2030/16; Y02E 10/52
See application file for complete search history.

(56) References Cited

U.S. PATENT DOCUMENTS

| | | | |
|---|---|---|---|
| 6,723,287 B1 * | 4/2004 | Ootatsume | G01N 21/253 198/465.2 |
| 7,193,205 B2 | 3/2007 | Remillard et al. | |
| 8,269,174 B2 | 9/2012 | Gardner et al. | |
| 8,648,906 B2 | 2/2014 | Delaney | |
| 9,131,196 B2 | 9/2015 | Lim et al. | |
| 2010/0104168 A1 | 4/2010 | Dobbe | |
| 2011/0017905 A1 | 1/2011 | Yeo | |
| 2012/0293796 A1 | 11/2012 | Ludowise et al. | |
| 2013/0132882 A1 | 5/2013 | Dussi et al. | |

FOREIGN PATENT DOCUMENTS

| | | |
|---|---|---|
| CN | 101067939 A | 11/2007 |
| CN | 102224260 A | 10/2011 |
| CN | 103649721 A | 3/2014 |
| CN | 104359841 A | 2/2015 |
| CN | 105389289 A | 3/2016 |
| CN | 205120577 U | 3/2016 |
| EP | 1 811 285 A1 | 7/2007 |
| EP | 2 829 866 A2 | 1/2015 |
| JP | 2000-258433 A | 9/2000 |
| WO | 2010/036829 A1 | 4/2010 |

OTHER PUBLICATIONS

Extended EP Search Report dated Jun. 3, 2019 of corresponding European Application No. 17831826.7, 6 Pages.

Lin Ping, titled "Design and Development of Automatic Spectrophotometer Control System", Computer Measurement & Control, Aug. 15, 2007, pp. 1014-1016.

* cited by examiner

OPTICAL AREA OF CUVETTES

PHOTOMETRIC CUVETTE MAPPING

CROSS-REFERENCE TO RELATED APPLICATIONS

This application claims the benefit of U.S. Provisional Application Ser. No. 62/365,287 filed Jul. 21, 2016, which is incorporated herein by reference in their entirety.

TECHNICAL FIELD

The present invention relates generally to methods, systems, and apparatuses for photometric cuvette mapping for use in in-vitro diagnostics system. The technology described herein may be applied to, for example, performing clinical laboratory in-vitro diagnostics in an automated testing environment.

BACKGROUND

In-vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers ("analyzers") onto which fluid containers, such as tubes or vials containing patient samples, have been loaded.

One component of the analyzer system is a reaction turntable that includes one or more reaction rings. Each reaction ring is arranged into multiple segments, with each segment containing multiple reaction vessels or "cuvettes." Photometer readings are taken at uniform spacing to calculate absorbance measurement in each cuvette. A design control or manufacturing issue of cuvette segments causes these vessels to be spaced unevenly or irregularly within and among segments, making it challenging (if not impossible) to get accurate photometer measurement.

SUMMARY

Embodiments of the present invention address and overcome one or more of the above shortcomings and drawbacks by providing methods, systems, and apparatuses related to photometric cuvette mapping. Using the techniques described herein, cuvette mapping is performed as an automatic alignment routine for each cuvette in the system. This mapping routine finds the optimal triggering point to generate precise photometric measurement. The routine may be performed as a part of the cuvette ring's initialization routine without any performance impact. Any new segments added can be automatically mapped during reset of the ring mechanism. As an added benefit of the techniques described herein, a reference measurement may be calculated between the cuvettes for dynamic source lamp referencing, thereby increasing the accuracy of the results.

According to some embodiments, a computer-implemented method for performing photometric cuvette mapping includes detecting edges associated with a plurality of gaps between a plurality of vessels in a reaction ring during a complete rotation of a reaction ring. Each gap is determined according to an edge detection process which includes identifying: a vessel interior in response to detection of a first predetermined number of photometer device control manager (DCM) measurements below a threshold value; a rising edge in response to detection of a second predetermined number of photometer DCM measurements above the threshold value; and identifying a falling edge in response to detection of a third predetermined number of photometer DCM measurements below the threshold value. The edge detection process further includes recording the rising edge and the falling edge as being indicative of one of the plurality of gaps. The edge detection process may be repeated until a predetermined number of gaps are determined (e.g., corresponding to expected values based on system design). Following the edge detection process, a plurality of trigger points may be computed for the plurality of vessels based on the recorded gaps. Then, indexing may be performed with the trigger points to collect photometric measurements.

In some embodiments of the aforementioned method, following identification of the vessel interior, if the rising edge is not identified within a fourth predetermined number of DCM measurements, a report of a missing edge may be generated and sent, for example, to a user. Similarly, following identification of the rising edge, a missing vessel report may be generated if the falling edge is not identified within a fourth predetermined number of DCM measurements.

In some embodiments of the aforementioned method, following the edge detection process flagging one or more vessels may be flagged as unusable for testing based on the recorded rising edges and the recorded falling edges. For example, in one embodiment, a vessel is designated as unusable for testing if at least one of the rising edge and the falling edge of a gap adjacent to the vessel is out of a predetermined tolerance.

Additional features, enhancements, and other modifications may be made to the aforementioned in different embodiments of the present invention. For example, in one embodiment, the photometer DCM uses a single wavelength to perform each of the photometer DCM measurements. In another embodiment, the recording of the rising edge and the falling edge are binarized with a threshold calculated from an initial set of measurements collected by the photometer DCM.

According to another aspect of the present invention, a computer-implemented method for performing photometric cuvette mapping includes aligning a reaction ring to a mechanical home position where a light associated with a photometer is between two vessels. The reaction ring is rotated past one rotation and edge data is read from the reaction ring using a photometer DCM, for example, using the edge detection process discussed above. The reaction ring is re-aligned to the mechanical home position and trigger points are computed from the edge data using the photometer DCM. Indexing is then performed with the trigger points to collect photometric measurements.

According to other embodiments of the present invention, a system for performing photometric cuvette mapping includes a photometer, a reaction ring, and a computer. The reaction ring is aligned to a mechanical home position where a light associated with a photometer is between two vessels. The computer uses the photometer to read edge data from the reaction ring using a DCM associated with the photometer. The computer next re-aligns the reaction ring to the mechanical home position and computes trigger points from the edge data using the DCM. Then, the computer indexes with the trigger points to collect photometric measurements with the photometer.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawing. For the purpose of illustrating the invention, there is shown in the drawing embodiments that are presently preferred, it being understood, however, that the invention is not limited to the specific instrumentalities disclosed. Included in the drawing are the following Figures.

DETAILED DESCRIPTION

The following disclosure describes the present invention according to several embodiments directed at methods, systems, and apparatuses related to photometric cuvette mapping. The tendency of the edges (leading and trailing) of a reaction ring vessel to block a light source is used to detect the vessel edges. Using the cuvette mapping techniques described herein, a photometer collects and analyzes the stream of readings, while the reaction ring makes a complete rotation after an initial homing. One wavelength (e.g., 596 nm) is used to detect the vessel edges. The data may be binarized (i.e., translated into a binary representation) with a threshold value (e.g., 90%) calculated from an initial set of readings. Cuvette mapping may be performed without any impact to the startup time of the instrument. Cuvette mapping provides a highly repeatable triggering point for photometric measurement. The techniques described herein also provide the optimal measurement area to oversample the input for high precision results.

Figure 1A:
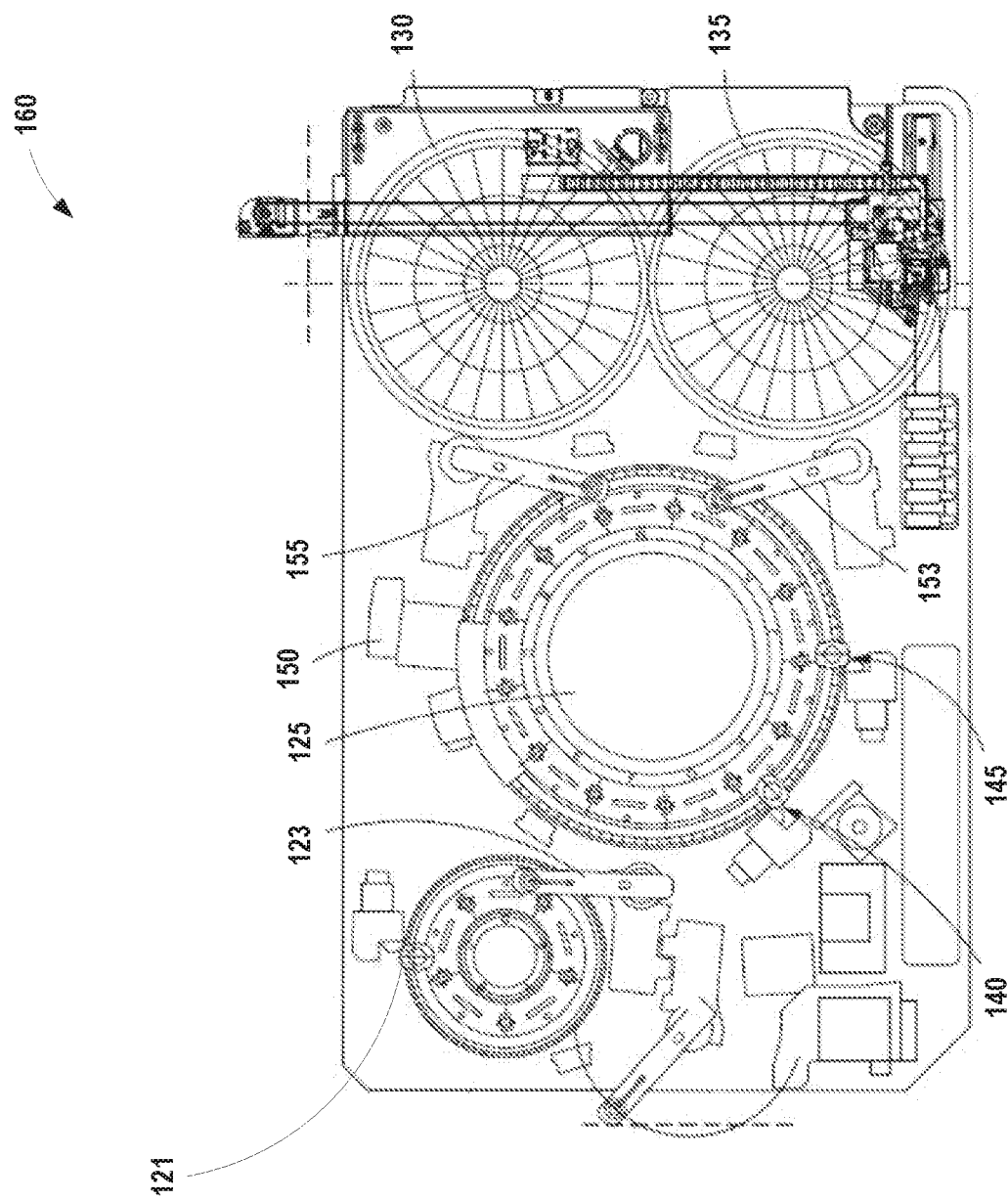
FIG. 1A is a top down view of electromechanical systems for an exemplary analyzer module for use with some embodiments.

To provide context to the present invention, FIG. 1A is a top down view of electromechanical systems for an exemplary analyzer module 160 for use with some embodiments. Sample arm 123 is responsible for aspirating a sample portion prepared by dilution mixer 121, moving above a reaction ring 125, and dispensing that sample portion into a cuvette. The reaction ring may include cuvette segment assembly as described below with respect to FIG. 1B. Reagents can be added before the sample arrives, or after the sample arrives via reagent arm 153 or reagent arm 155. Reagent servers 130 and 135 include a variety of different reagents, allowing a variety of tests to be performed by analyzer module 160. Reagent arms 153 and 155 move aliquots of reagents from reagent server 135 or reagent server 130, respectively. These aliquots are then dispensed into cuvettes in reaction ring 125. Reaction ring 125 moves cuvettes in a predetermined sequence such that each cuvette reaches reagent mixer 140 or sample mixer 145 for mixing. Once mixed, the reaction between the sample and reagent proceeds in the cuvette. Reaction ring 125 rotates to allow photometer 150 to take photometric measurements of the reaction at predetermined times.

Figure 1B:
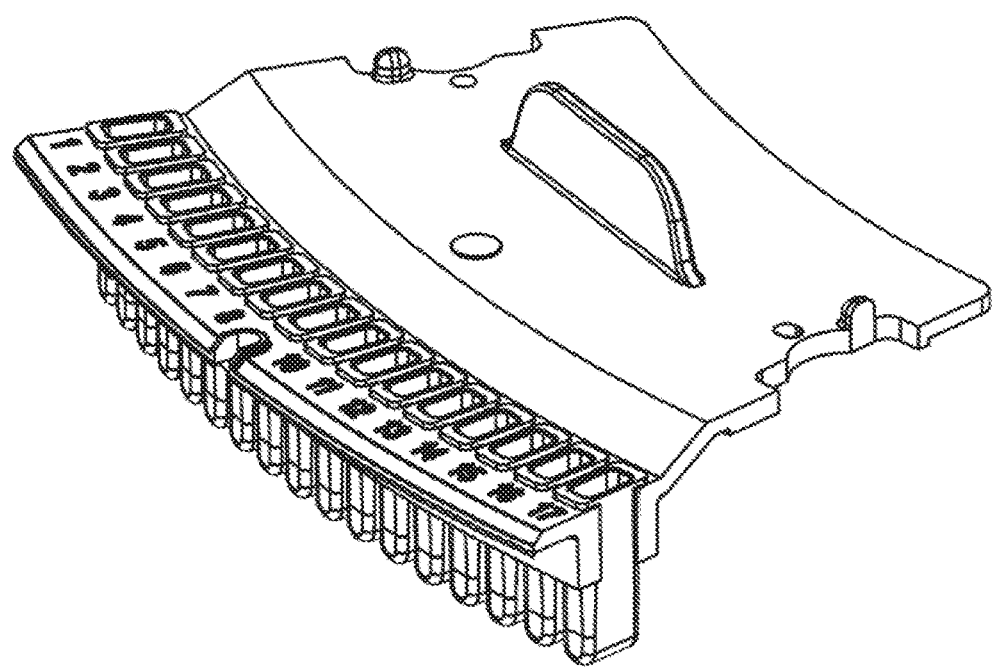
FIG. 1B shows a view of an example cuvette segment assembly with cuvettes installed in a side view.
Figure 1C:
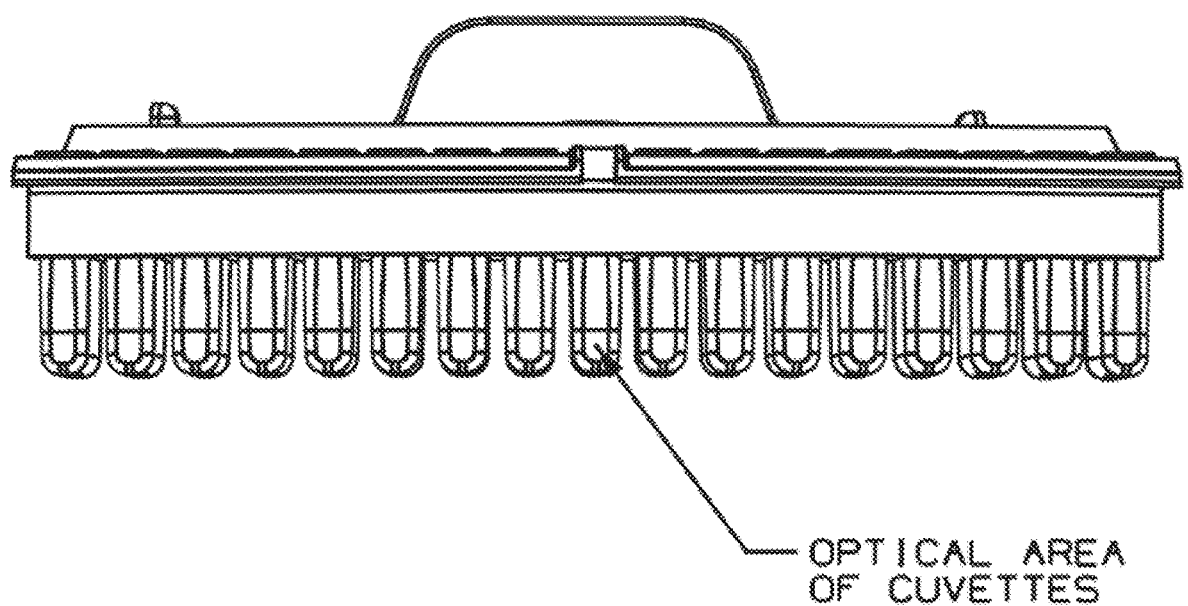
FIG. 1C shows a view of an example cuvette segment assembly with cuvettes installed in a front view.

An analyzer reaction ring comprises a plurality of cuvettes organized across a plurality of segments. FIGS. 1B and 1C show a view of an example cuvette segment assembly with cuvettes installed in a side and front view, respectively. Each cuvette is a small tube designed to hold samples for spectroscopic experiments. Cuvettes are sealed at one end and have a circular cross-section or, as illustrated in FIG. 1B the cross section may be square or rectangular. Square or rectangular cross-sections are generally used to avoid refraction artefacts while making photometric measurements. Various materials may be used to construct cuvettes including, without limitation, optical glass, UV quartz, IR quartz, or sapphire. FIG. 1C shows an alternative view of the view shown in FIG. 1B. The view provided in FIG. 1B illustrates that the lower portion of each cuvette includes a small window referred to herein as the "optical area". During the photometric measurement, light emitted by the photometer is directed to the optical area of the cuvette.

Photometer readings are triggered at uniform spacing on the breadboard design. A design control or manufacturing issue of some cuvette segments causes these vessels to be spaced unevenly or irregularly within and among segments. There is no pattern to the spacing. The techniques described herein provide a cuvette mapping process that may be implemented in any combination of hardware and software to map the triggering point dynamically. The tendency of the edges (leading and trailing) of the reaction ring vessel to block the light source is used to detect the vessel edges. The gaps between the edges are not uniform. Software for controlling the photometer, referred to herein as the "Photometer Device Control Manager (DCM)" collects and analyzes the stream of measurements, while the reaction ring makes a complete rotation slowly after an initial homing. One wavelength is used to detect the vessel edges and the data get binarized with a threshold calculated from an initial set of measurements. Thus, values above the threshold are set to one value (e.g., "1"), while values below the threshold are asset to another value (e.g., "0"). In some embodiments, the aforementioned wavelength is 596 nm and the threshold is 90%.

The DCM measurements rise and fall between zero and positive values. The transition of the signal that rises to a peak is referred to as a "rising edge," while the transition of the signal that falls from the peak is referred to as the "falling edge." A rising edge of the gap that is the trailing edge of the vessel is used to calculate the "trigger point" of that vessel. A rising edge can happen only due to an absence of obstruction, while a falling edge can be due to any obstruction, including debris or bubble. The falling edge is de-bounced longer to avoid noise. The rising edge is checked against a window (e.g., 5%) and will be flagged if it falls out of this tolerance window.

A final check of edge detection may be carried out at the host computer level, and vessels will be flagged as unusable if the edges are detected out of tolerance. The term "flagging" in this context means creating a record that the vessel is unusable. Prior to using the vessel during testing, this record is read by the analyzer and only vessels not designated as unusable will be filled with samples, etc. The flag may also be used to generate an alert or other message (e.g., log file entry) to notify users that the vessel is not usable.

The main controller (host computer) that coordinates the devices (DCMs) also controls the "offset" into the vessels to trigger photometer measurements. Reference measurements are taken at every gap, and one filtered reference measurement is sent to the host for absorbance calculation. The entire routine of edge detection may be completed in a relatively brief time period (e.g., around 20 seconds in some implementations), including homing the reaction ring before and after. The "bad" vessels are flagged as un-usable and this mapping routine may be called every time a reaction ring gets ready for reservation processing.

A host can integrate cuvette mapping into its overall photometric measurement process as follows. Initially, the reaction ring is aligned to the mechanical home position where the photometer light beam will be in between two reaction vessels. This is the ring's home position (0). Next, the photometer encoder is reset to 0, and the host commands the Photometer DCM to capture edge data. Then, the host slowly rotates the reaction ring past one rotation (e.g., 223 slots) and reads the edge data from the Photometer DCM. Subsequently, the host re-homes the ring and asks the Photometer DCM to compute trigger points from the edges detected (as described in further detail below with reference to FIG. 2). The host can then start indexing to collect photometric measurements based on those trigger points. Horizontal alignment to the photometer is eliminated. All probes can be aligned to the ring at its mechanical home position, and the photometer is aligned to the reaction ring (vessel and gap for reference) automatically.

Figure 2:
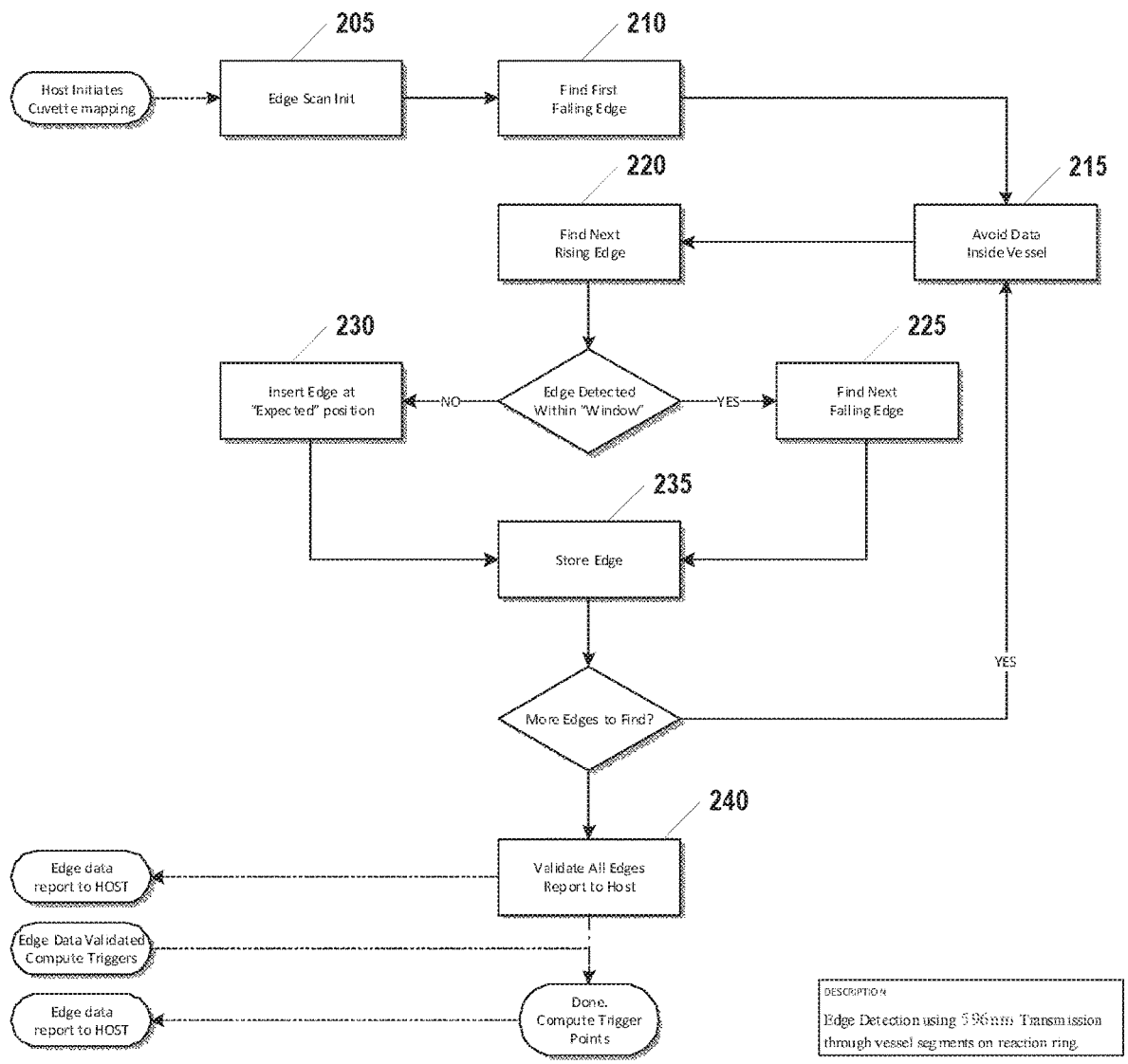
FIG. 2 illustrates a cuvette mapping process that may be performed by a Photometer Device Control Manager (DCM), according to some embodiments.

FIG. 2 illustrates a cuvette mapping process 200 that may be performed by a Photometer DCM, according to some embodiments. The term cuvette mapping, as used herein, refers to the process of identifying where the cuvettes are located on the reaction ring and where gaps between cuvettes are located. It should be noted that certain numerical values are provided herein as examples of the measurements that may be gathered and utilized during the cuvette mapping process 200; however, it should be understood that other values may be used for these measurements in other embodiments of the present invention. Starting at step 205, edge scan initialization procedure is performed during which operational counters are initialized. During step 205, the photometer encoder may be configured to trigger conversions every 20 encoder counts until the threshold value is calculated from the first 200 points.

Continuing with reference to FIG. 2, the first falling edge is detected at step 210. Measurements are performed at step 210, confirming that the above threshold value is seen within the first 2000 encoder counts, and the below threshold value is seen in the next 2000 encode counts. Based on the measurements, the DCM latches the falling edge transition position. Next, at step 215, to avoid data in the vessel interior, the system confirms that the below threshold value is seen consecutively 26 times from 2000 encoder counts away from the last falling edge that was detected. The term "vessel interior," as used herein refers to the portion of the vessel between the two edges. At step 220, the next rising edge is found. During step 220, the system latches to the rising edge. The DCM waits for a minimum "50" count wide high level. If there is not a rising edge within 4000 encoder counts from the last falling edge, a report may be issued indicating that an edge is missing. This report may take various forms including, without limitation, a message sent to the host computer or a remote computer for display and/or recording (e.g., in a log file). This message may designate relevant information such as the time, clinical test information, and/or the location of the missing edge with respect to the reaction ring.

If an edge is detected within the "window," the next falling edge is detected at step 225, and the system latches to the falling edge. The DCM waits for a minimum count wide low level (e.g., 500). If a falling edge is not detected within 4000 encoder counts from the last rising edge, a missing cuvette report may be issued. This report may take various forms including, without limitation, a message sent to the host computer or a remote computer for display and/or recording. These contents of the report may designate relevant information such as the time, clinical test information, the location of the cuvette with respect to the reaction ring, and/or a cuvette identifier. Conversely, if an edge is not detected within the "window," step 230, an edge is inserted at the "expected" position. Next, at step 235, the DCM saves the rising edge and the falling edge of the current gap between cuvettes. The DCM then determines whether the edge scan is complete. In some embodiments, the edge scan is deemed completed if a certain number of gaps are found (e.g. corresponding to the number of vessel locations in the vessel ring assembly on the reaction ring). For example, in one embodiment, the scan is complete if 221 gaps are found. In other embodiments, the scan is complete once the first measured gap is measured for a second time. If there are more edges to find, the cuvette mapping process 200 may be repeated starting at step 215. Conversely, if there are no other additional edges to be detected, the edges are validated and reported to the host at step 240.

Figure 3A:
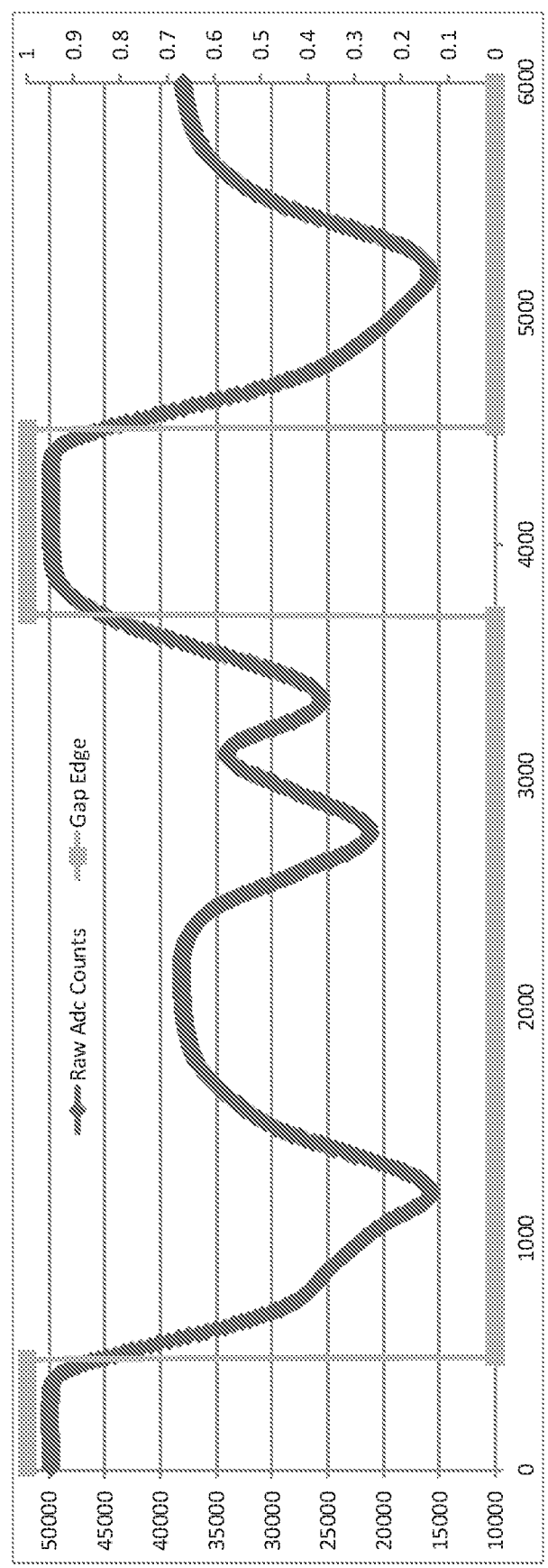
FIG. 3A illustrates how light transmission through a vessel may be correlated to gap edges during performance of a cuvette mapping process according to the techniques described herein.
Figure 3B:
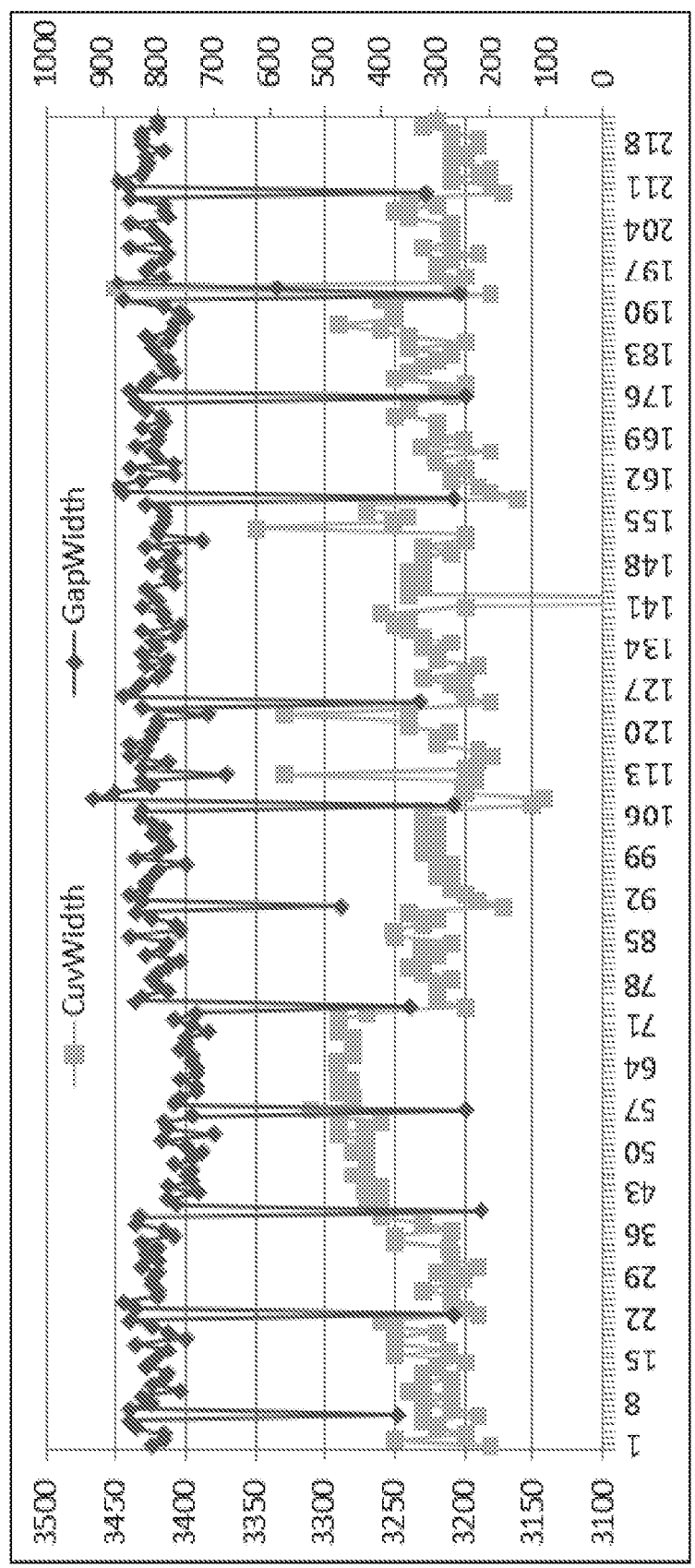
FIG. 3B illustrates sample edge detection results that may be generated using a cuvette mapping process.
Figure 3C:
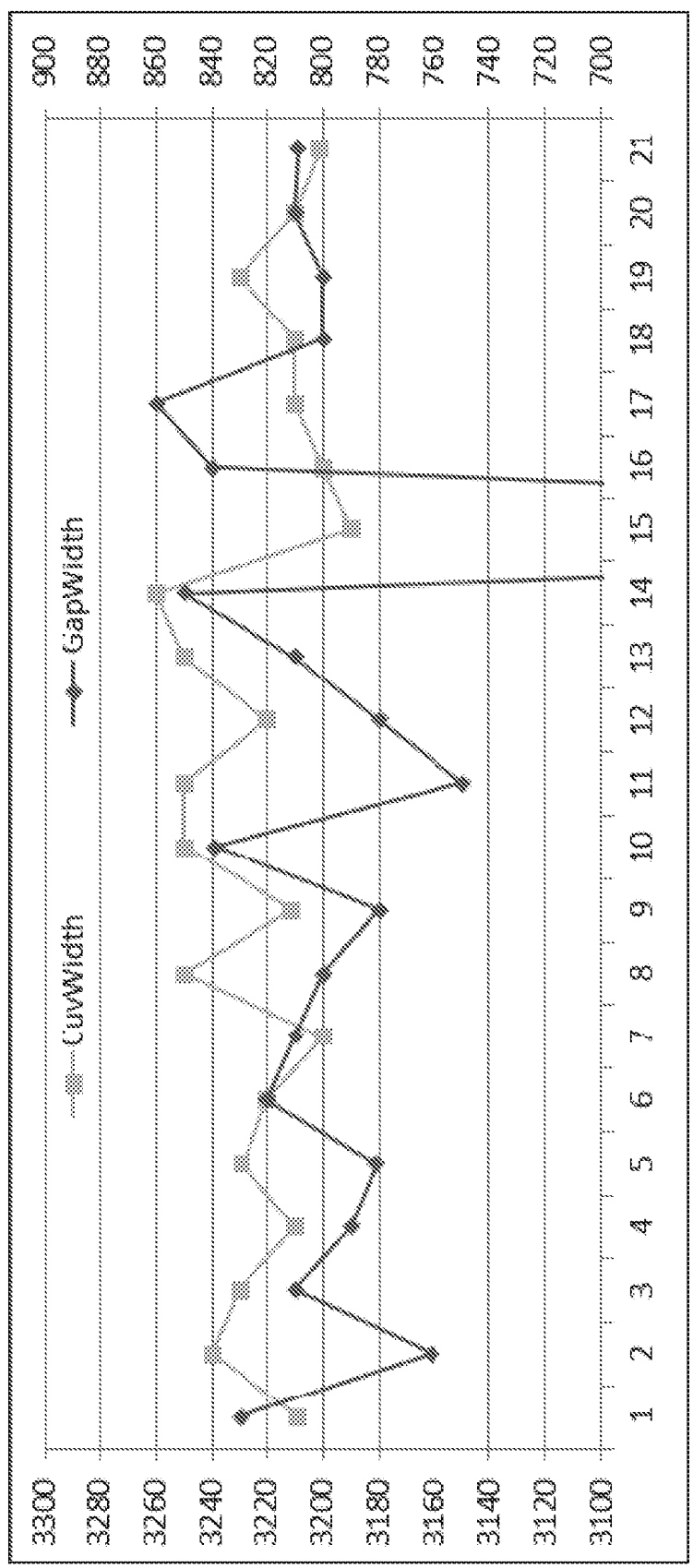
FIG. 3C provides a detailed view of edges 10-30 shown in FIG. 3B.

FIG. 3A illustrates how light transmission through a vessel (as determined by encoder counts) may be correlated to gap edges during performance of a cuvette mapping process according to the techniques described herein. FIG. 3B illustrates sample edge detection results that may be generated using such a process. In this example, the gap between cuvettes is normally around 800 counts, except in between segments it is approximately 300. The variation in a vessel's inside width is due to the variation of angular placement of the vessel in its slot. FIG. 3C provides a detailed view of edges 10-30.

Figure 4A:
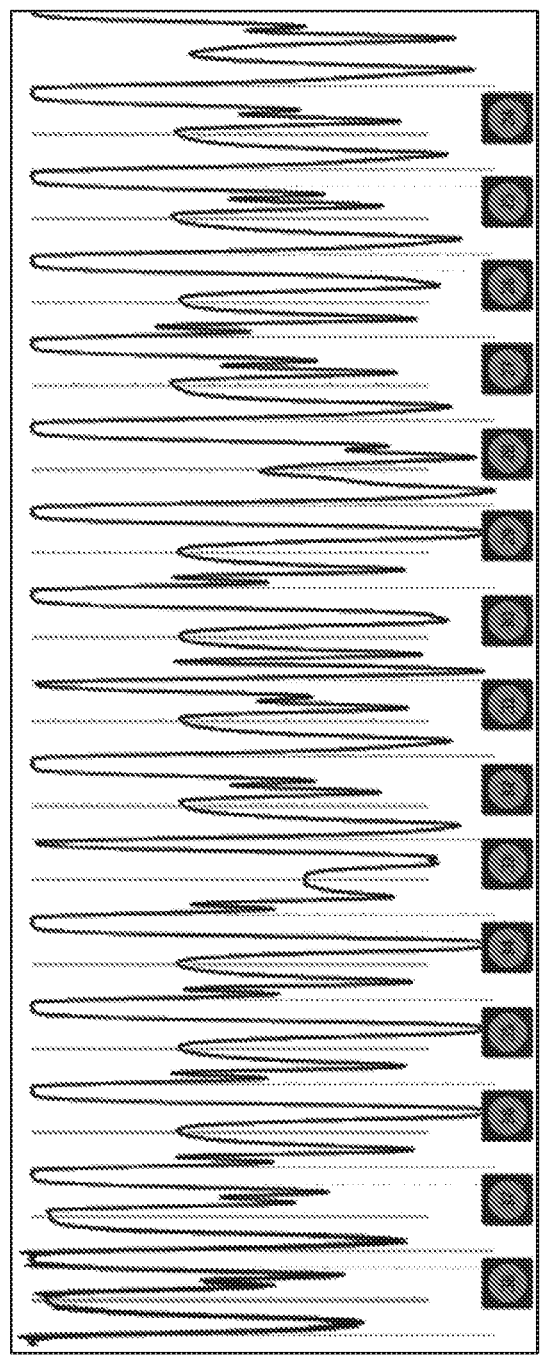
FIG. 4A shows a snapshot of the data collected during a typical execution of the process, according to some embodiments.
Figure 4B:
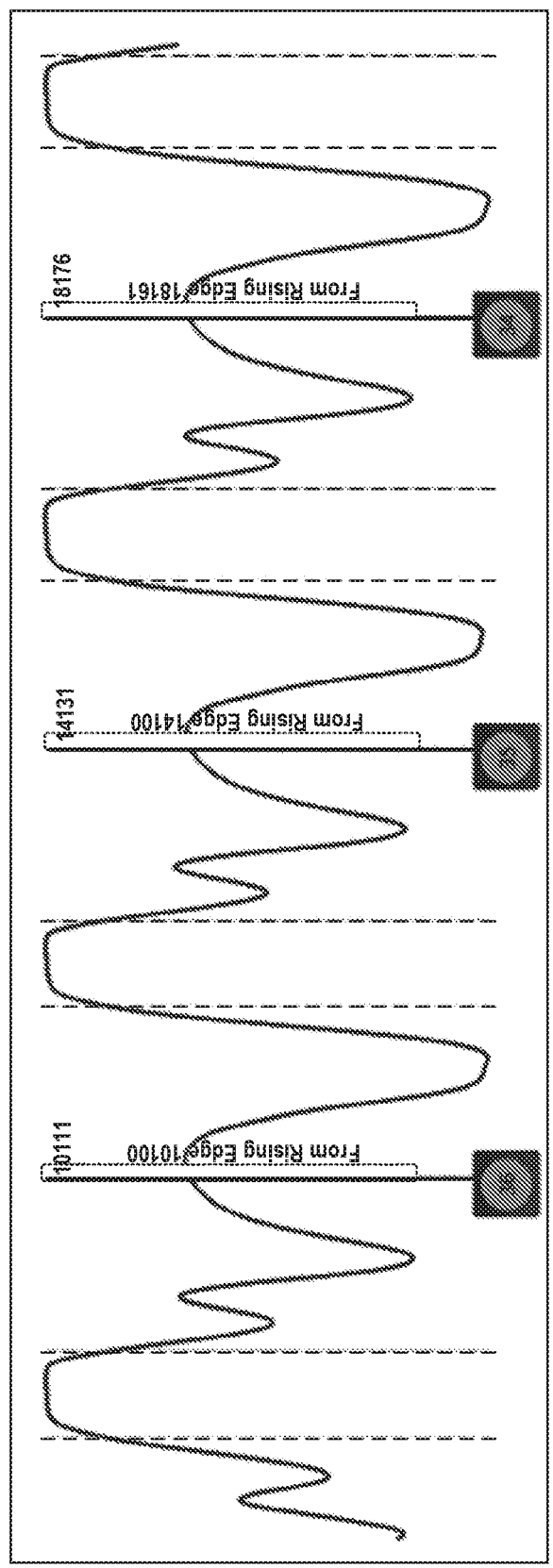
FIG. 4B provides a detailed view of a several edges shown in FIG. 4A.
Figure 4C:
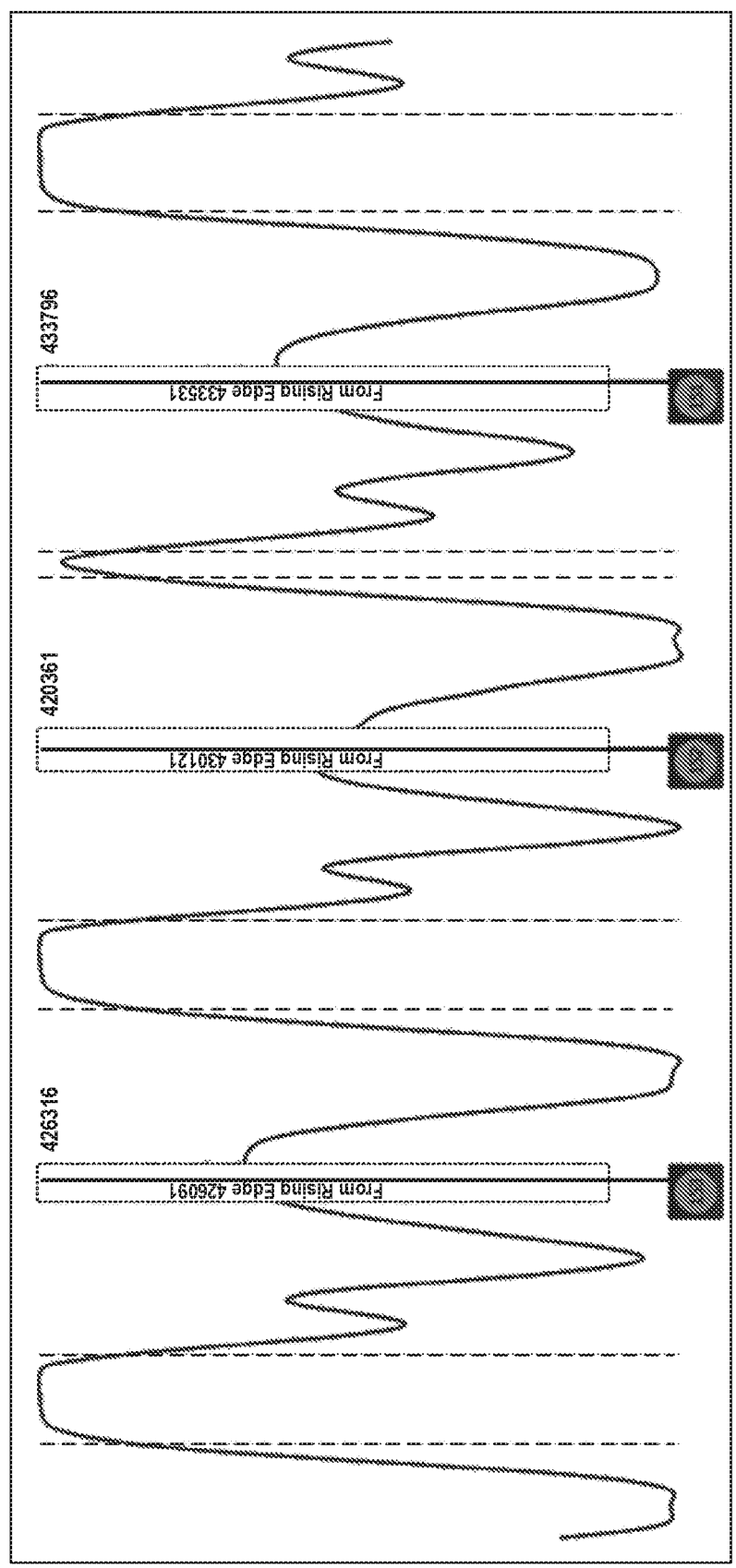
FIG. 4C illustrates the short gap between segments.
Figure 4D:
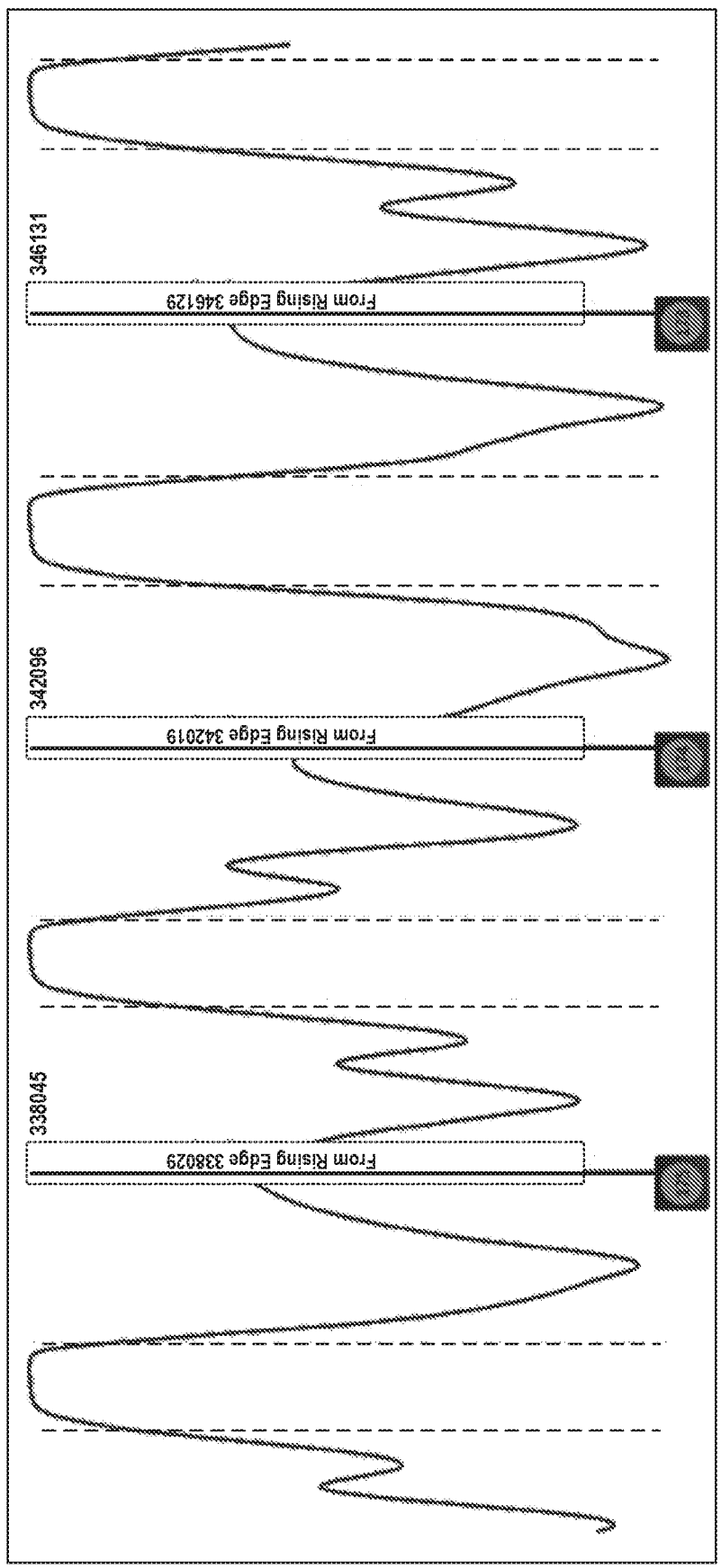
FIG. 4D provides an example of an uneven gap.
Figure 4E:
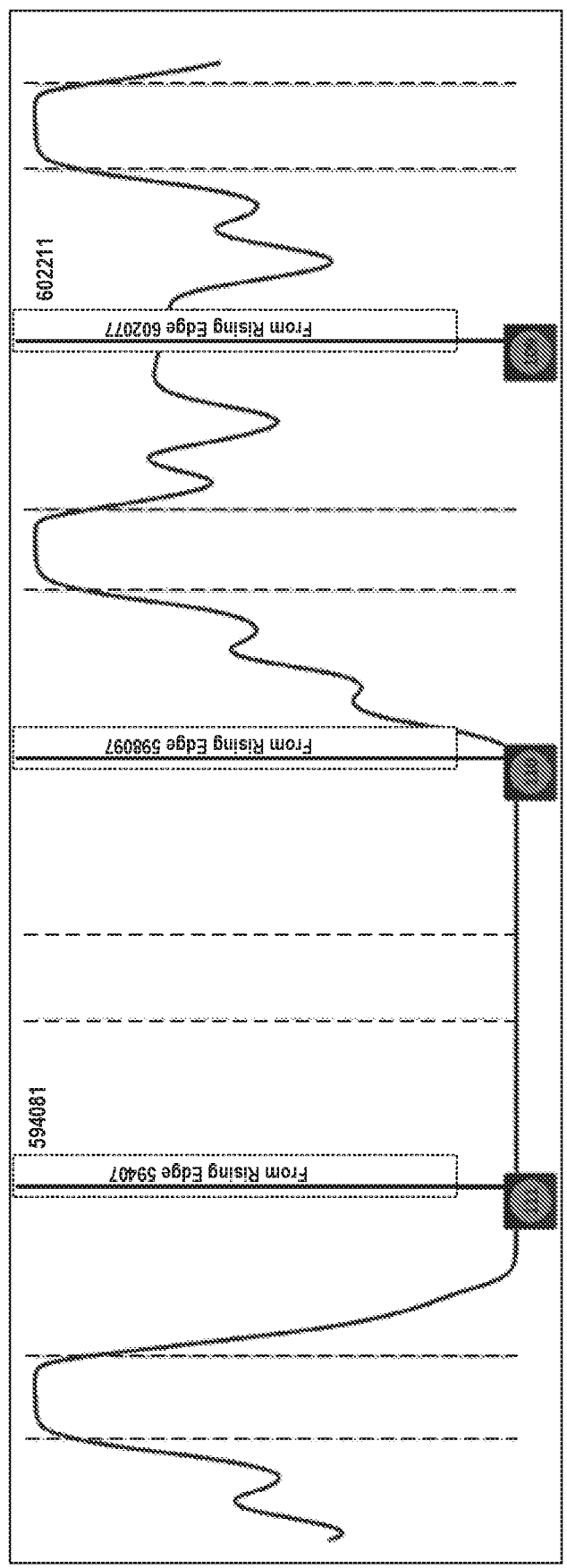
FIG. 4E shows an example in which one gap is masked off, but the next edge is detected correctly, as may be implemented in a cuvette mapping process according to the techniques described herein.
Figure 4F:
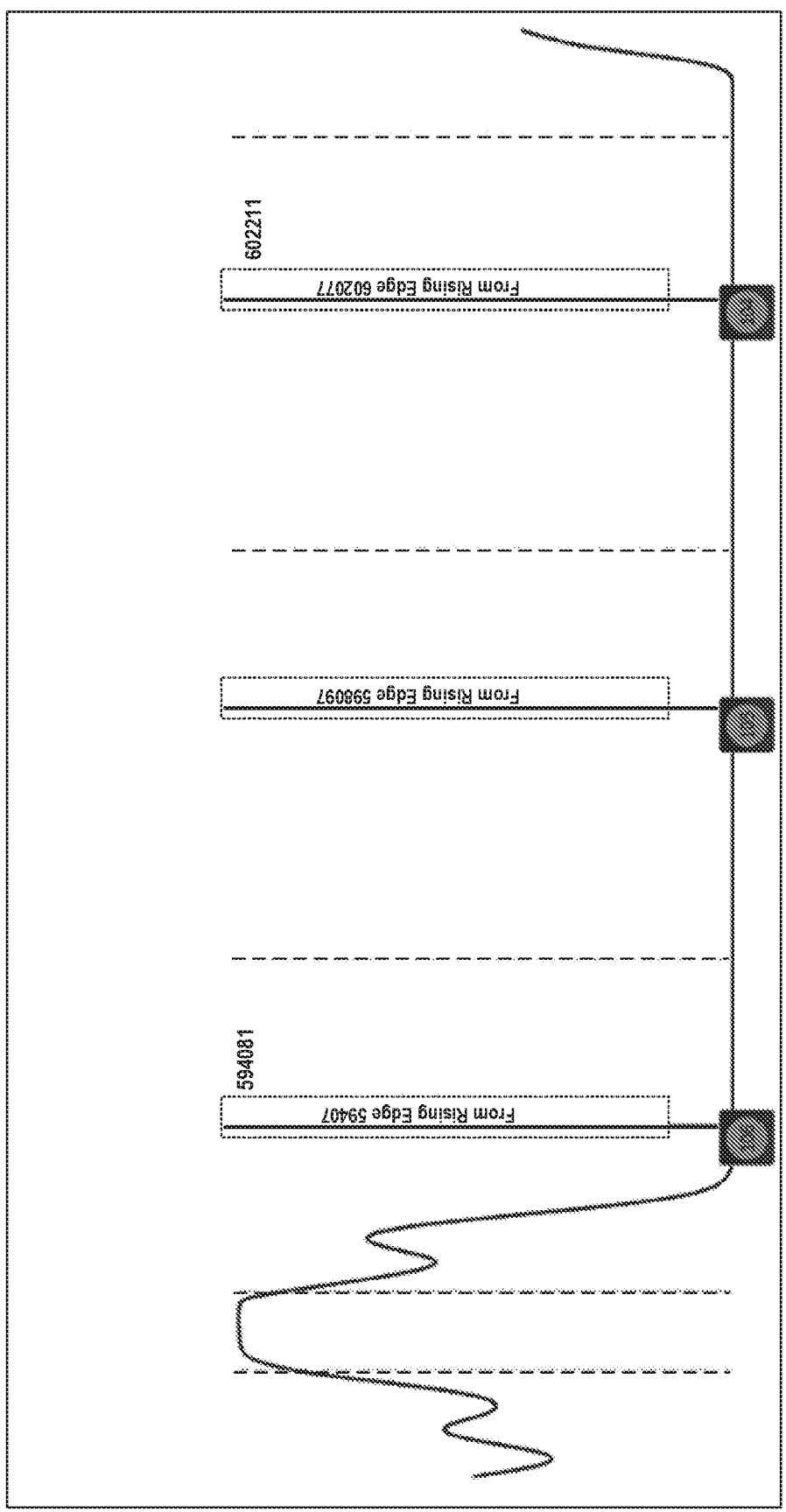
FIG. 4F depicts how multiple consecutive gaps may be masked off and the next gap edge is still detected correctly using the techniques described herein.
Figure 4G:
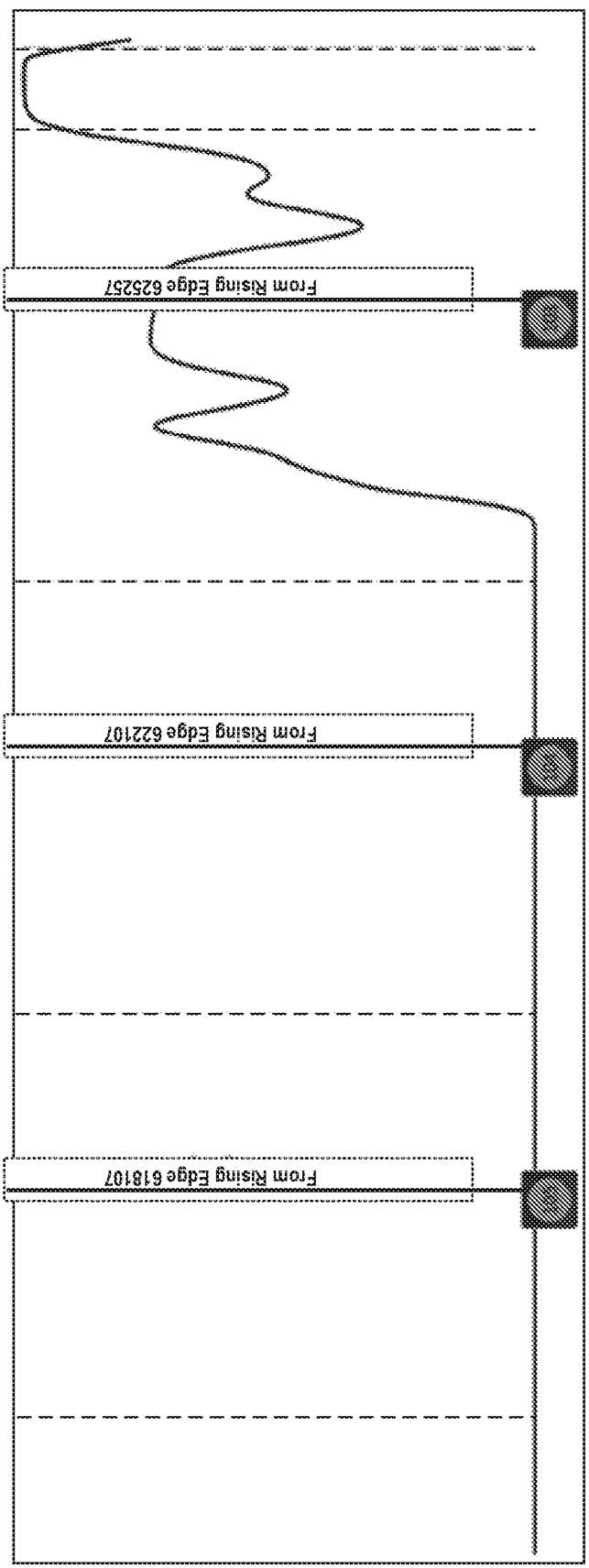
FIG. 4G provides a continuation of the visualization shown in FIG. 4F.
Figure 4H:
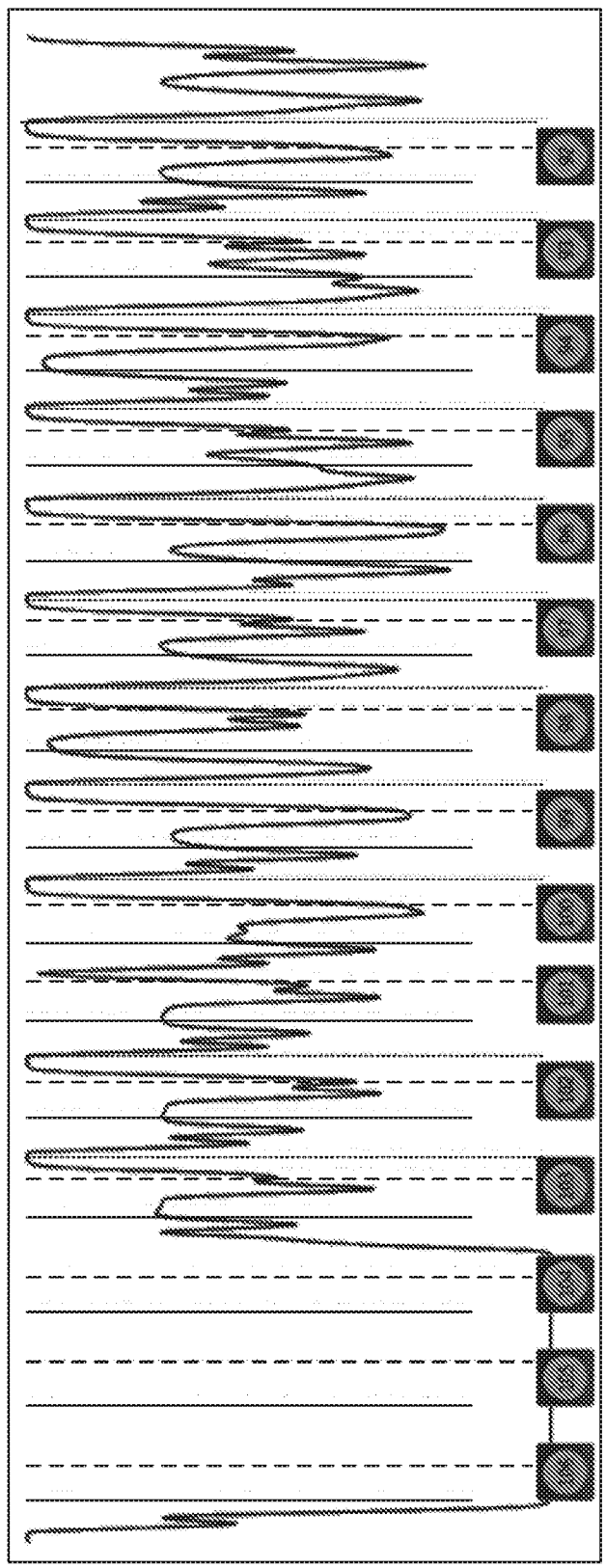
FIG. 4H provides an additional view where three gaps are masked off.

FIGS. 4A-4G provides an example visualization of data collected during a cuvette mapping process, according to some embodiments of the present invention. FIG. 4A shows a snapshot of the data collected during a typical execution of the process. FIG. 4B provides a detailed view of a several edges. FIG. 4C illustrates the short gap between segments. FIG. 4D provides an example of an uneven gap. FIG. 4E shows an example in which one gap is masked off, but the next edge is detected correctly. FIGS. 4F and 4G (which should be viewed as continuous) depict how multiple gaps (3 in this example) may be masked off, and the next gap edge is still detected correctly using the techniques described herein. FIG. 4H provides an additional view where three consecutive vessels are masked off.

Figure 5:
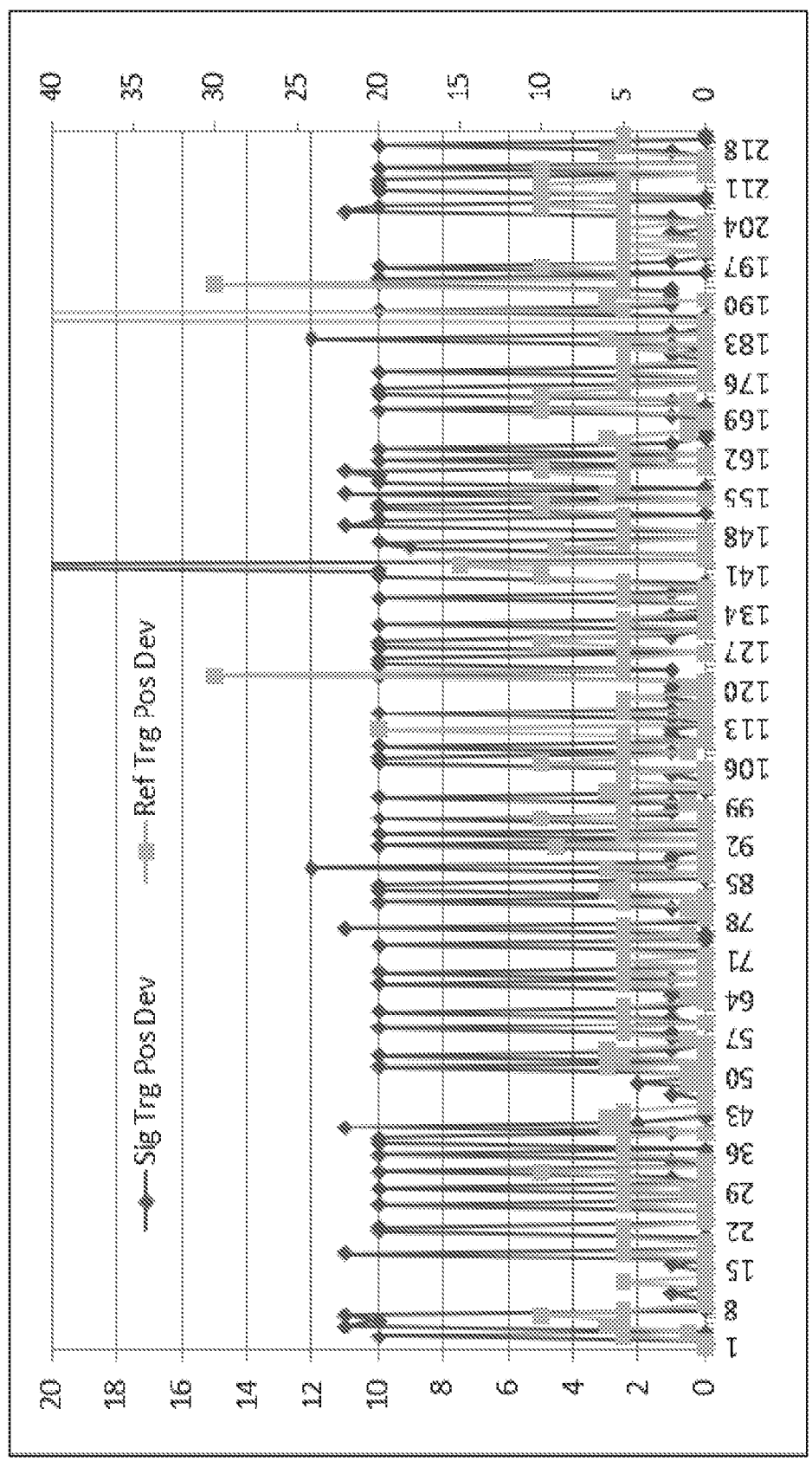
FIG. 5 provides an illustration of additional mapping test results generated using a cuvette mapping process, according to the techniques described herein.

FIG. 5 provides an illustration of additional mapping test results generated using a cuvette mapping process, according to the techniques described herein. More specifically, the edges detected and the calculated trigger points for cuvettes in a segment are depicted in FIG. 5. The scan resolution in this example is 10 encoder counts. The outliers are caused by the (simulated) missing edge tests.

Figure 6A:
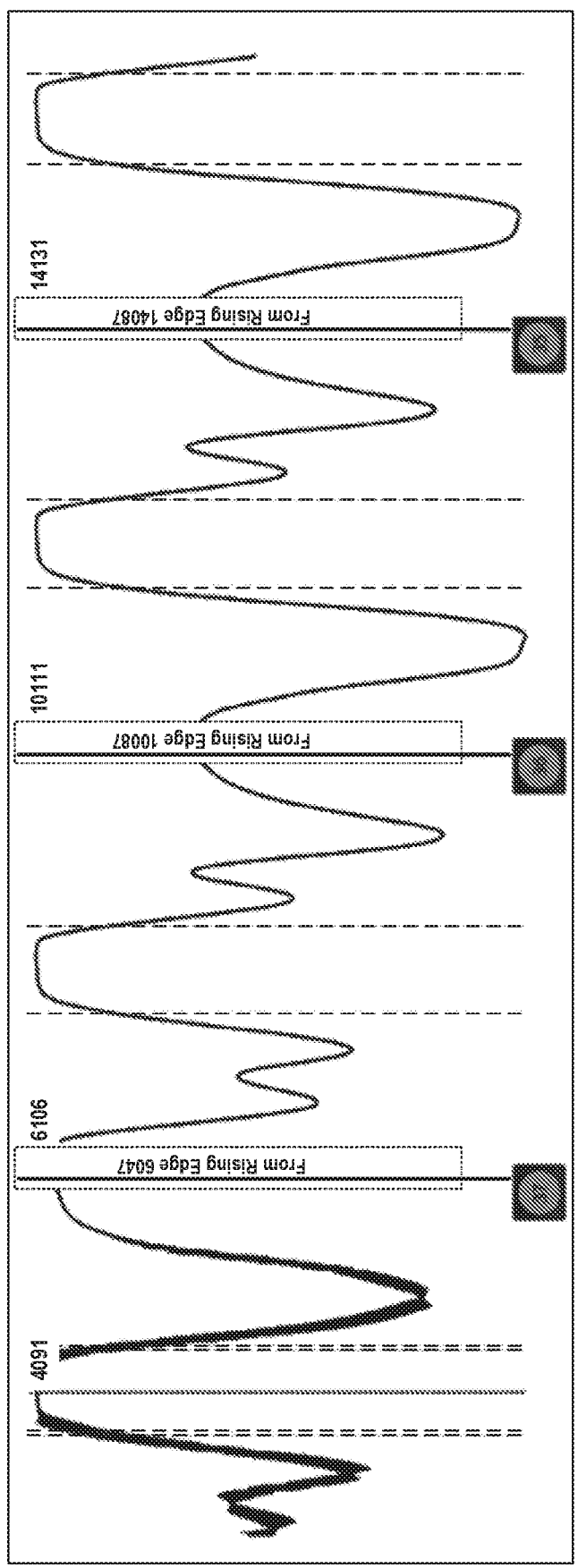
FIG. 6A shows sample results generated when one vessel is filled with water.
Figure 6B:
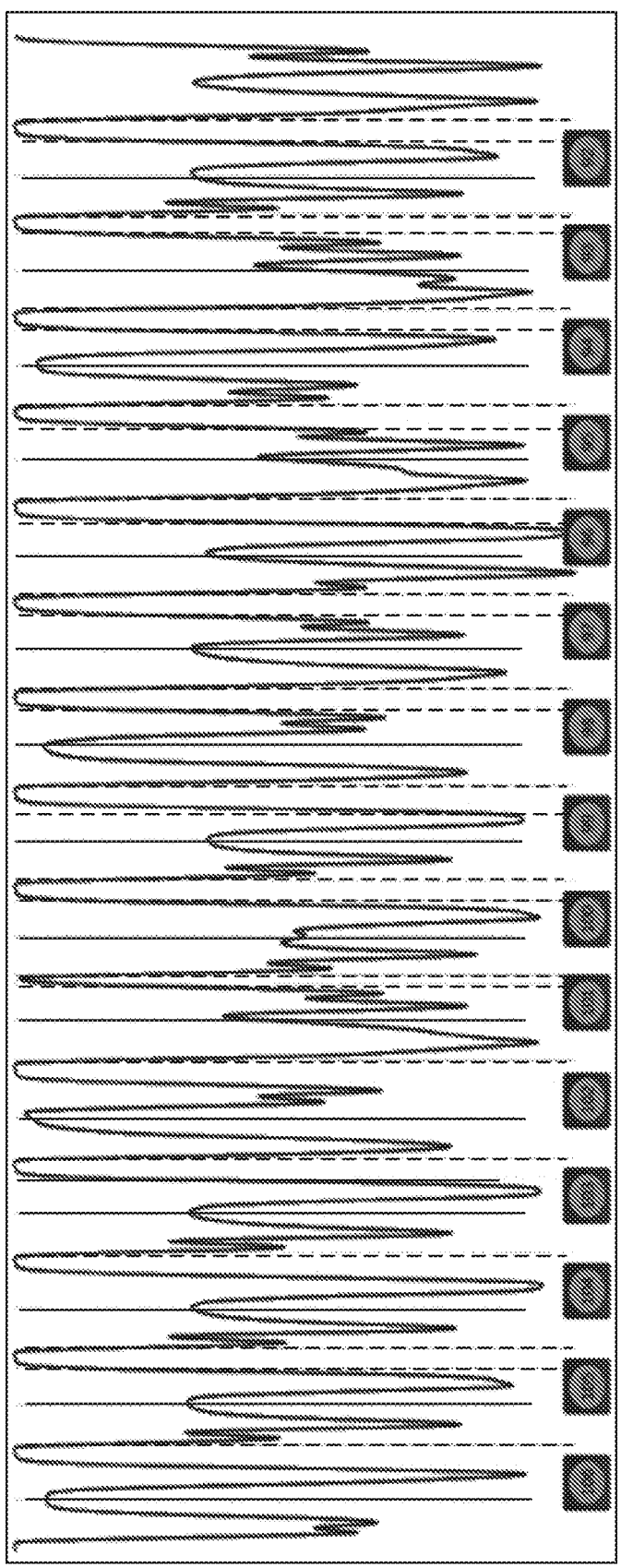
FIG. 6B shows sample results generated when multiple vessels are filled with water.
Figure 6C:
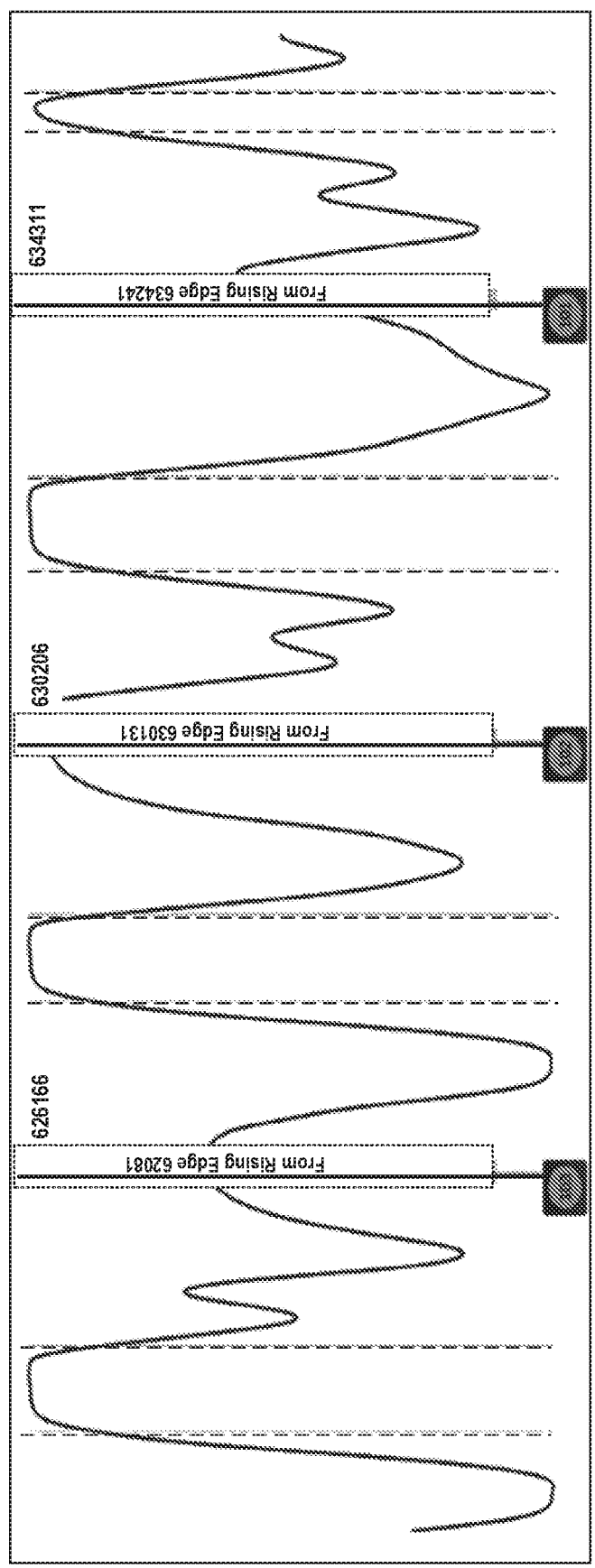
FIG. 6C provides additional results from this testing depicted in FIG. 6B.

FIGS. 6A-6C illustrate that vessels transmit better when filled with clear water. FIG. 6A shows sample results generated when one vessel (marked 37 in the small boxes shown in FIG. 6A) is filled with water. FIG. 6B shows sample results generated when multiple vessels (marked 106, 102, 98, and 94 in the small boxes shown in FIG. 6B) are filled with water. FIG. 6C provides additional results from this testing.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes, and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A computer-implemented method for performing photometric cuvette mapping, the method comprising:

during a complete rotation of a reaction ring, detecting edges associated with a plurality of gaps between a plurality of vessels in a reaction ring, wherein each gap is determined according to an edge detection process comprising:
identifying a vessel interior in response to detection of a first predetermined number of photometer device control manager (DCM) measurements below a threshold value;
identifying a rising edge in response to detection of a second predetermined number of photometer DCM measurements above the threshold value;
identifying a falling edge in response to detection of a third predetermined number of photometer DCM measurements below the threshold value; and
recording the rising edge and the falling edge as being indicative of one of the plurality of gaps.

2. The method of claim 1, further comprising:
following identification of the vessel interior, if the rising edge is not identified within a fourth predetermined number of DCM measurements, generating a report of a missing edge.

3. The method of claim 1, further comprising:
following identification of the rising edge, if the falling edge is not identified within a fourth predetermined number of DCM measurements, generating a report of a missing vessel.

4. The method of claim 1, further comprising:
following the edge detection process, computing a plurality of trigger points for the plurality of vessels based on the recorded gaps.

5. The method of claim 4, further comprising:
indexing with the trigger points to collect photometric measurements.

6. The method of claim 1, wherein the edge detection process is repeated until a predetermined number of gaps is determined.

7. The method of claim 1, further comprising:
following the edge detection process flagging one or more vessels as unusable for testing based on the recorded rising edges and the recorded falling edges.

8. The method of claim 6, further comprising:
designating a vessel as unusable for testing if at least one of the rising edge and the falling edge of a gap adjacent to the vessel is out of a predetermined tolerance.

9. The method of claim 1, wherein the photometer DCM uses a single wavelength to perform each of the photometer DCM measurements.

10. The method of claim 1, further comprising:
binarizing the recording of the rising edge and the falling edge with a threshold calculated from an initial set of measurements collected by the photometer DCM.

11. A computer-implemented method for performing photometric cuvette mapping, the method comprising:
aligning a reaction ring to a mechanical home position where a light associated with a photometer is between two vessels;
rotating the reaction ring past one rotation;
reading edge data from the reaction ring using a photometer device control manager (DCM);
re-aligning the reaction ring to the mechanical home position;
computing trigger points from the edge data using the photometer DCM; and indexing with the trigger points to collect photometric measurements, wherein the edge data corresponds to a plurality of gaps between a plurality of vessels in the reaction ring and the edge data is read from the reaction ring for each gap according to an edge detection process comprising, identifying a vessel interior in response to detection of a first predetermined number of photometer DCM measurements below a threshold value, identifying a rising edge in response to detection of a second predetermined number of photometer DCM measurements above the threshold value, identifying a falling edge in response to detection of a third predetermined number of photometer DCM measurements below the threshold value, and recording the rising edge and the falling edge as being indicative of one of the plurality of gaps.

12. The method of claim 11, further comprising:

following identification of the vessel interior, if the rising edge is not identified within a fourth predetermined number of DCM measurements, generating a report of a missing edge.

13. The method of claim 11, further comprising:

following identification of the rising edge, if the falling edge is not identified within a fourth predetermined number of DCM measurements, generating a report of a missing vessel.

14. The method of claim 11, wherein the edge detection process is repeated until a predetermined number of gaps is determined.

15. The method of claim 11, further comprising:

following the edge detection process flagging one or more vessels as unusable for testing based on the recorded rising edges and the recorded falling edges.

16. The method of claim 15, further comprising:

designating a vessel as unusable for testing if at least one of the rising edge and the falling edge of a gap adjacent to the vessel is out of a predetermined tolerance.

17. The method of claim 11, wherein the photometer DCM uses a single wavelength to perform each of the photometer DCM measurements.

18. The method of claim 11, further comprising:

binarizing the recording of the rising edge and the falling edge with a threshold calculated from an initial set of measurements collected by the photometer DCM.

* * * * *